United States Patent [19]

Kitzinger

[11] 4,181,699

[45] Jan. 1, 1980

[54] APPARATUS FOR DETECTING THE PRESENCE OF A SPECIFIC SUBSTANCE IN A GAS STREAM

[75] Inventor: Frank Kitzinger, Montreal, Canada

[73] Assignee: Noranda Mines Limited, Toronto, Canada

[21] Appl. No.: 884,173

[22] Filed: Mar. 7, 1978

[51] Int. Cl.$^2$ .............................................. G01N 21/30
[52] U.S. Cl. .......................................... 422/87; 422/91
[58] Field of Search ............. 23/232 R, 232 E, 254 R, 23/254 E, 255 R, 255 E, 253 TP; 422/87, 91, 119, 56, 57

[56] References Cited

U.S. PATENT DOCUMENTS

| 2,762,568 | 9/1956 | Sullivan | 23/255 E X |
| 2,812,243 | 11/1957 | Goody | 23/255 R |
| 4,023,930 | 5/1977 | Blunck et al. | 23/254 E X |
| 4,032,297 | 6/1977 | Lyshkow | 23/254 E |
| 4,073,621 | 2/1978 | Bull et al. | 23/254 E |

*Primary Examiner*—Joseph Scovronek
*Attorney, Agent, or Firm*—Fleit & Jacobson

[57] ABSTRACT

An apparatus for detecting the presence of a specific substance in a gas stream is disclosed. The apparatus comprises a sensing chamber adapted to receive a test paper which is subject to coloration when contacted by a specific substance in a gas contained in the sensing chamber, means for generating a light beam and directing it toward the test paper in the sensing chamber, a light beam sensing device responsive to the extent to which the test paper in the sensing chamber undergoes coloration in response to exposure to the specific substance in the gas stream, an amplifier connected to the light beam sensing device for providing an output voltage which is proportional to the coloration of the test paper, and means connected to the amplifier for providing an output signal which is an instantaneous indication of the concentration of the substance to be monitored, comprising a signal conditioning circuit connected to the amplifier for providing an output which is a linear function of the cumulative amount of the substance to be detected contacting the test paper, and a differentiator responsive to the output of said amplifier for deriving the instantaneous concentration of the substance in the gas stream. The apparatus is further provided with a beam splitter for dividing the light beam into two separate beams, one directed toward the test paper in the sensing chamber and the other toward a variable optical density filter, and a second light beam sensing device responsive to the transmittance of the variable optical density filter. The amplifier is responsive to the two light beam sensing devices for providing an output which is a function of the ratio of the light sensed by the two light sensing devices irrespective of the light source intensity variations. An automatic zero adjustment device is also provided for resetting the output of the amplifier to zero prior to taking measurements.

12 Claims, 5 Drawing Figures

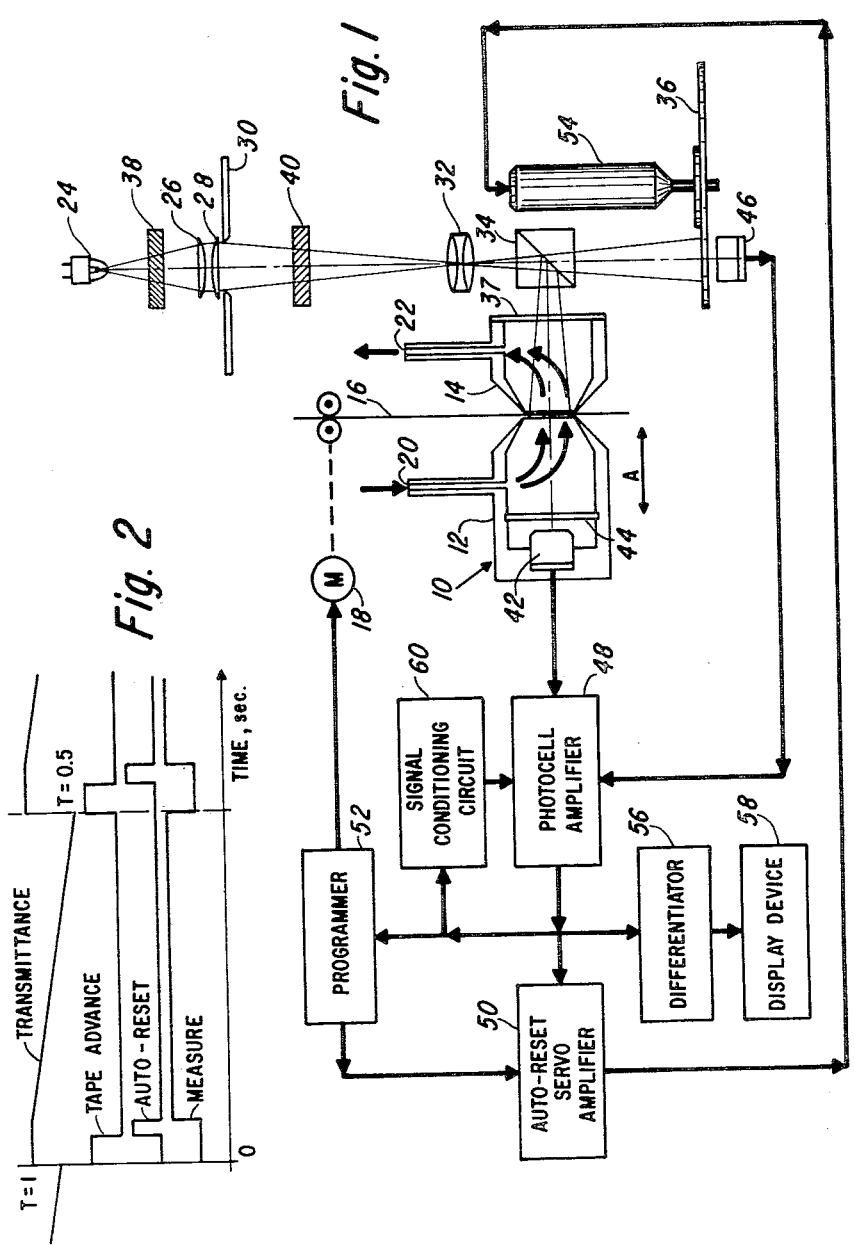

APPARATUS FOR DETECTING THE PRESENCE OF A SPECIFIC SUBSTANCE IN A GAS STREAM

This invention relates to an apparatus for detecting the presence of a specific substance in a gas stream using reagent test papers.

It is generally known to use the coloration of a reagent test paper for determining the presence of a gas or a gas component in a gas mixture or air. Known apparatus, such as that disclosed in U.S. Pat. Nos. 4,023,930 issued May 17, 1977 and 4,032,297 issued June 28, 1977, generally uses a lamp as a light source for illuminating a test paper placed in a measuring chamber through which the gas to be monitored is circulated, and a light sensing means such as a photocell for detecting the increasing light absorption of the test paper due to coloration of the test paper in response to exposure to the gas. The known apparatus simply all provides an output which is a non-linear indication of the cumulative amount of gas reacted with the test paper due to the Bouguer and Lambert exponential law of light absorption. They are normally set to operate an alarm when a predetermined amount of gas to be detected has been reached. None of the known apparatus provides an instantaneous indication of the concentration of the gas to be monitored as it is passed through the instrument.

Another drawback of the known apparatus is that they are not provided with automatic zero adjustment prior to taking a reading and must therefore be adjusted manually.

Still another drawback of the known apparatus is that they are not compensated for lamp ageing and lamp voltage fluctuations.

Still another drawback of the existing apparatus is that the tape is heated by the lamp which normally acts as a light source and this adversely affects the accuracy of the coloration of the tape particularly at the end of the measuring cycle.

It is therefore the object of the present invention to provide an apparatus which is substantially free of the above mentioned drawbacks and which, more particularly, provides an instantaneous indication of the concentration of the substance to be monitored.

The apparatus, in accordance with the invention comprises a sensing chamber adapted to receive a test paper which is subject to coloration when contacted by a specific substance in a gas contained in the chamber, means for generating a light beam and directing it toward the test paper in the sensing chamber, a light beam sensing device responsive to the extent to which the test paper in the sensing chamber undergoes coloration in response to exposure to the specific substance in the gas stream, an amplifier connected to the light beam sensing device for providing an output voltage which is proportional to the coloration of the test paper, and means connected to the amplifier for providing an output signal which is an instantaneous indication of the concentration of the substance to be monitored.

The apparatus is preferably provided with a beam splitter for dividing the light beam into two separate beams, one directed toward the test paper in the sensing chamber and the other toward a variable optical density filter, and a second light beam sensing device responsive to the transmittance of the variable optical density filter. The amplifier (hereinafter referred to as a photocell amplifier) is responsive to the two light beam sensing devices for providing an output which is a function of the ratio of the light sensed by the two light sensing devices irrespective of the light source intensity variations.

An automatic zero adjustment device is also preferably provided for resetting the output of the photocell amplifier to zero prior to taking a measurement.

The means for providing an output signal which is an instantaneous value of the concentration of the substance to be monitored preferably comprises a signal conditioning circuit connected to the photocell amplifier for causing the photocell amplifier to provide an output which is a linear function of the cumulative amount of the substance reacted with the reagent paper, and a differentiator connected to the output of the photocell amplifier for deriving the instantaneous concentration of the substance. Such signal conditioning circuit may be an operational amplifier having its output connected to the input of the photocell amplifier and provided with positive feedback from the output of the photocell amplifier so as to vary the input of the photocell amplifier in a direction such as to render its output linear, whereby differentiation of the linear output of the photocell amplifier will provide an instantaneous indication of the concentration of the substance to be detected.

A low pass filter is preferably connected to the output of the photocell amplifier for eliminating the noise components of the output signal.

The apparatus also preferably comprises a decomposition compensator interconnecting the photocell amplifier to the differentiator for compensating for the usual decomposition of the substance reacted with the reagent paper.

In order to prevent the heat generated by the lamp acting as a light source from adversely affecting the test paper, a heat filter is located in the path of the light beam, preferably between the lamp and the beam splitter.

A filter is also preferably located in the light beam ahead of the beam splitter for passing light of a predetermined wavelength. Such filter may be an interference filter or an optical glass filter. The use of a selective filter is important in order to maintain high sensitivity for sensing specific colorations.

The test paper normally consists of a strip of predetermined length which is good for several readings. Therefore, it is normally arranged to be intermittently fed through the sensing chamber for taking a series of measurements. A motor is therefore preferably provided in the apparatus for advancing the test paper. In order to permit advancement of the paper, the measuring chamber is divided in two sections, one of which is movable by a suitable mechanism preferably connected with the motor driving the tape. The apparatus is preferably provided with a programmer which sequentially energizes the motor for a short period of time to advance the tape, then the automatic zero adjustment means for a short time interval to reset the apparatus to zero, and finally operates a pump for feeding the gas stream into the measuring chamber.

The variable optical density filter may be a disc the transmittance of which may be varied over a range corresponding to that of a typical reagent test paper. Such a disc may be attached to the shaft of a servo motor operated by the above mentioned automatic zero adjustment means. Alternatively, the variable optical density filter may be a strip of predetermined length advanced by a linear servo motor. The automatic zero adjustment means may comprise an operational amplifier connected to the output of the photocell amplifier, and switch means responsive to the programmer for interconnecting the operational amplifier and the servo motor. Thus, during the automatic zero adjustment time period, the servo motor is operated to set the output of the photocell amplifier to zero.

The photocell amplifier may comprise an operational amplifier having the first light sensing device connected in series with its inverting input terminal and the second light sensing device connected across its inverting input terminal and its output terminal for automatically adjusting the gain of the photocell amplifier to be a function of the ratio of the light sensed by the two light sensing devices irrespective of the light source intensity variations, a voltage reference source, a summing network for comparing the output of the operational amplifier to the reference source, and an inverter connected to the output of the summing network for providing the output signal of the photocell amplifier.

The invention will now be disclosed, by way of example, with reference to a preferred embodiment illustrated in the accompanying drawings in which:

FIG. 1 illustrates a block diagram of an apparatus in accordance with the invention;

FIG. 2 illustrates a diagram of the sequence followed by the programmer;

Figure 3:
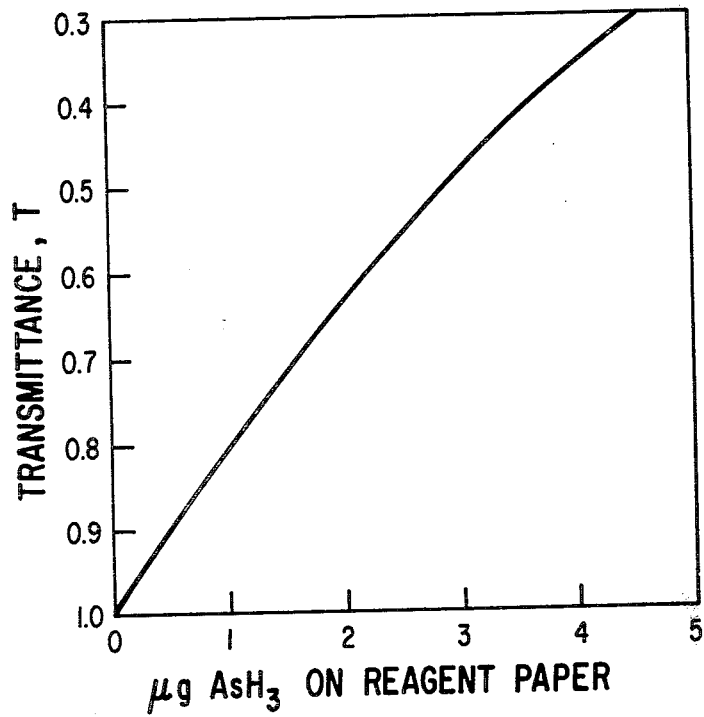
FIG. 3 illustrates the transmittance of the reagent test paper as a function of the amount of substance reacted with it.

Referring to FIG. 1, there is shown a measuring chamber made of two sections 12 and 14. Section 12 is movable as indicated by arrow A so as to permit a reagent test paper 16 to be advanced through the chamber by means of a motor 18. The movement of section 12 is preferably controlled by motor 18 through a conventional coupling mechanism (not shown). The gas stream containing the substance to be detected is fed through inlet 20 in section 12 of the chamber by means of a suitable pump (not shown) and exits through the outlet 22 in section 14 of the chamber. An O-ring or other suitable means (not shown) is located between the two sections of the chamber to ensure sealing of the chamber during measurement.

The portion of the test paper in the measuring chamber is illuminated by a light beam originating from a lamp 24 acting as a light source. The light beam is formed by plane-convex lenses 26 and 28 located just ahead of an apertured plate 30. An image of the light beam passing through apertured plate 30 is formed by an achromatic lens 32 and a beam splitter 34 on both the test paper 16 and on a variable optical density filter 36. Various optical arrangements may be used for forming the above images. As an example, the distance between the apertured plate and the achromatic lens may be arranged to be twice the focal length f of the lens. Similarly, the distance between the achromatic lens and the beam splitter plus the distance between the beam splitter and the test paper, or between the beam splitter and the variable optical density filter may be adjusted to be equal to 2f. An achromatic lens is used in order to prevent chromatic aberration as commonly known. The end of chamber section 14 is closed by a transparent plate 37 so as to permit the light beam to go through.

A heat filter 38 is located between the heat source 24 and the lenses 26 and 28 to prevent heat from the lamp from affecting the moisture content of the test paper. This has been found to greatly influence the accuracy of the reading, particularly at the end of the measuring period because the paper is gradually dried by the heat generated by the lamp. Of course the heat filter may be located anywhere between the light source and the beam splitter.

A filter 40 which may be an interference filter or an optical glass filter is positioned ahead of the beam splitter for passing a colour of a predetermined wavelength. For example, if the coloration to be observed on the test paper is yellow, a blue filter is advantageously used. It is very important that the filter be located ahead of the beam splitter so as to equally affect both photocells. The use of a selective filter is important in order to maintain high sensitivity for sensing specific colorations.

Figure 4:
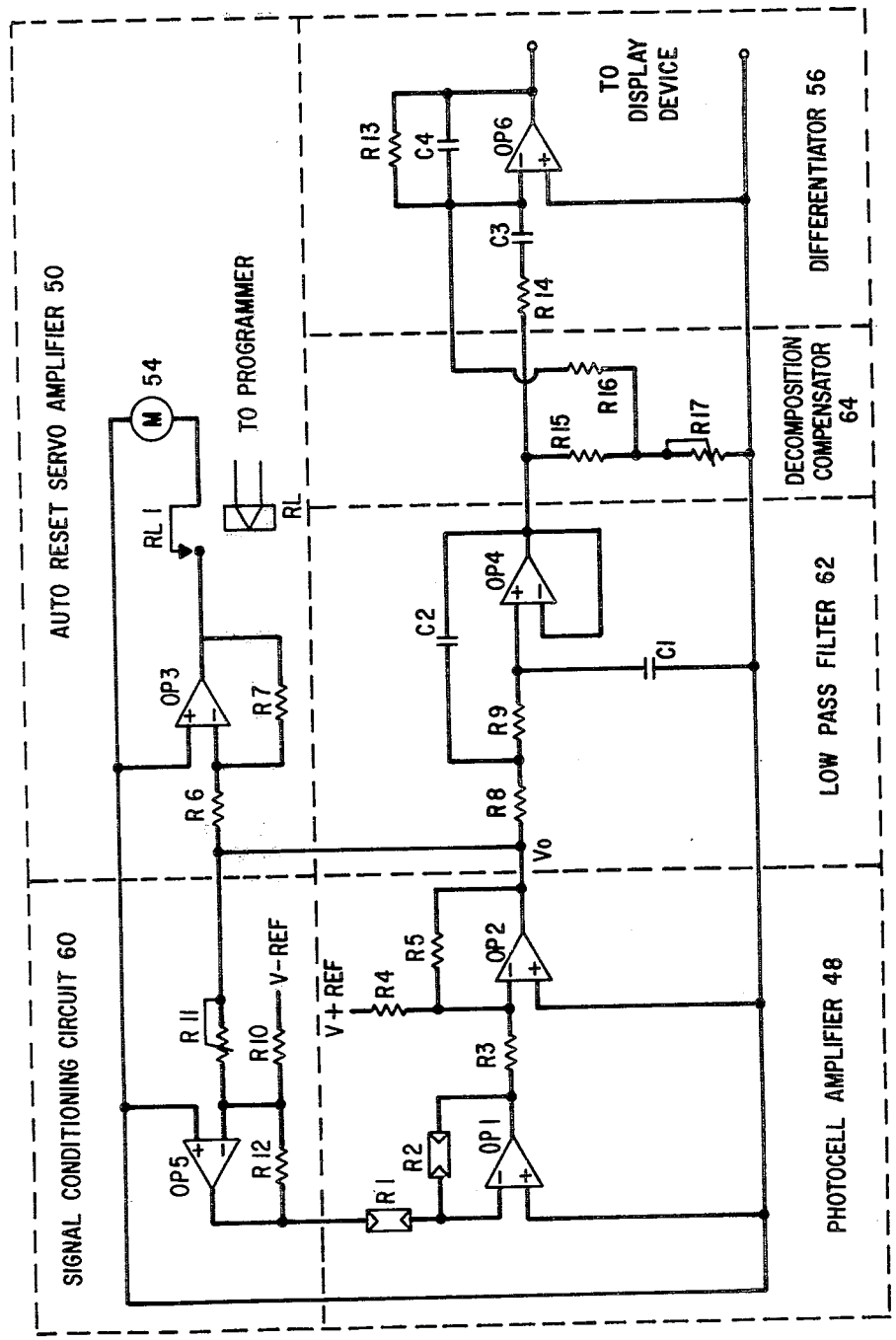
FIG. 4 illustrates a circuit diagram of the electrical components of the apparatus of FIG. 1.

The light passing through test paper 16 is detected by a photocell 42 located behind a transparent plate 44 in section 12 of the chamber. Similarly, the light passing through variable optical density filter 36 is detected by photocell 46 located behind the variable optical density filter 36. It is to be understood that other light sensing devices responsive to the light passing through or reflected by the test paper or the variable optical density filter are also envisaged. Photocells 42 and 46 are variable impedance devices which are connected to the circuit of a suitable photocell amplifier 48 to provide an output which is proportional to the coloration of the test paper and is a direct ratio of the light sensed by the two photocells irrespective of the light source intensity variations, such as caused by lamp ageing and lamp voltage fluctuations. One example of such an amplifier is illustrated in FIG. 4 and will be disclosed in detail later. Let us say for now that, when the transmittance of the variable optical density filter 36 is matched with that of the test paper (with no gas flowing through the measuring chamber) the impedance of both photocells 42 and 46 is equal and the output of the photocell amplifier is zero. This zero volt output indicates a condition hereinafter referred to as a transmittance value of 1 prior to feeding of the gas being monitored through the measuring chamber. If the transmittance of the variable optical density filter does not exactly match that of the test paper as it should prior to feeding the gas to be monitored through the chamber, photocell 46 will have an impedance different from that of photocell 42 and the output of the photocell amplifier 48 will be different from zero. Such output is fed to an auto-reset servo amplifier 50 which is referred to previously as an automatic zero adjustment device. The output of the servo amplifier is fed under the control of a programmer 52 to a servo motor 54 driving variable optical density filter 36. Thus, if the output of the photocell amplifier is not zero prior to feeding gas to the measuring chamber, servo motor 54 will automatically rotate variable optical density filter 36 so as to match the transmittance of such optical density filter with that of the paper and thereby automatically bring the output of the amplifier back to zero.

The programmer 52 is a conventional timing device adapted to switch on the motor 18, the servo motor 54 and the gas pump (not shown) following the sequence shown in FIG. 2. For a predetermined time interval of say 20 sec, motor 18 is operated to open the chamber 10 and advance the tape. The motor is then stopped and the chamber closed. Servo amplifier 50 is subsequently connected to servo motor 54 to effect automatic zero output adjustment of the amplifier 48. A time interval of 1-10 sec is believed to be sufficient to perform this adjustment. Servo motor 54 is then deenergized and the pump controlling the feed of the gas into the measuring chamber is operated to initiate the measuring cycle which is carried out for a predetermined period of time which is preferably until a condition of 0.5 transmittance through the test paper is reached, or for a preselected time period of say 2-8 hrs if the gas sample does not contain any significant amount of the substance to be detected.

During the measuring period, the presence of the substance to be detected, such as arsine gas in air, for example, will gradually change the colour of a test paper such as one impregnated with mercuric bromide, from white to yellow. When illuminated by a blue light beam (using a blue filter), such colour change will reduce the transmittance of the paper and the impedance of the photocell 42 will be increased while the impedance of the photocell 46 will not change. This will cause the output of the photocell amplifier to increase to a value corresponding to the cumulative amount of arsine reacted with the test paper. The curve of FIG. 3 illustrates the transmittance of the reagent test paper as a function of the amount of arsine in $\mu g$ reacted with the reagent paper. This curve is not linear due to the Bouguer and Lambert exponential law of light absorption and the output of the photocell amplifier, in the absence of any compensation, would also be non-linear. As it will be disclosed more fully later, it is the object of the invention to differentiate the output signal of the photocell amplifier by means of a suitable differentiator 56 to provide an instantaneous indication of the concentration of the substance as it is reacted with the test paper and to show this concentration on a display device such as shown by block 58. However, since the output of the photocell amplifier would not be linear, the differentiation of such output would not provide a true indication of the concentration of the substance reacted with the test paper. In order to cause the amplifier 48 to produce a linear output, it is proposed, in accordance with the invention, to provide a signal conditioning circuit 60 which is connected to the output of the photocell amplifier for compensating for the non-linearity of transmittance of the reagent test paper due to the exponential law of light absorption. An example of a signal conditioning circuit will be disclosed fully in the following description of FIG. 4.

Referring now to FIG. 4, there is shown an embodiment of a circuit diagram including the photocell amplifier 48, the auto-reset servo amplifier 50, the differentiator 56, the signal conditioning circuit 60 and further comprising a low pass filter 62 and a decomposition compensator 64.

The photocell amplifier consists of an operational amplifier OP1 having its inverting input terminal connected to a source of positive voltage (provided by signal conditioning circuit 60 to be disclosed later) through light sensitive resistor R1 (photocell 42 of FIG. 1). The non-inverting terminal of the operational amplifier is connected to ground. A light sensitive resistor R2 (photocell 46 of FIG. 1) is connected in the feedback loop of the operational amplifier between its inverting input terminal and its output terminal. When the transmittance of the variable optical density filter 36 is matched with that of the test paper (with no gas flowing through the measuring chamber), R1=R2 and the output of the operational amplifier is the reverse of the voltage applied to R1. The output of the operational amplifier OP1 is fed to the inverting input terminal of an operational amplifier OP2 acting as an inverter through a first resistor R3 of a summing network including a second resistor R4 having one terminal connected to a reference source V+REF and a second terminal connected to the inverting input terminal of the inverter OP2. Under the condition of 1.0 transmittance, the reference voltage V+REF is chosen so that 0 volt is applied to the inverting input terminal of the inverter OP2 and thus an output voltage $V_0=0$ appears at its output. A resistor R5 is connected between the output terminal of inverter OP2 and its inverting input terminal to determine the gain of the inverter is known manner. The non-inverting input terminal of the operational amplifier is connected to ground.

When the transmittance of the variable optical density filter 36 does not match that of the test paper (prior to feeding gas through the chamber) impedance R2 (photocell 46) has a value different from impedance R1 (photocell 42) and the output of the operational amplifier OP1 and thus of the inverter OP2 is different from 0. Such output is fed to the inverting input terminal of an operational amplifier OP3, acting as a comparator, through a resistor R6. The non-inverting input terminal of operational amplifier OP3 is connected to ground. A resistor R7 is connected between the inverting input terminal of the operational amplifier and its output to determine the gain of the operational amplifier in known manner. The non-inverting input terminal of the operational amplifier OP3 is connected to ground. The output of the operational amplifier OP3 is applied to servo motor 54 (FIG. 1) through the contacts RL-1 of a relay RL energized by programmer 52 (FIG. 1). Operational amplifier OP3 is the auto-reset servo amplifier 50 of FIG. 1, and operates motor 54 to rotate variable optical density filter 36 in one direction or the other depending on the polarity of the error voltage appearing at the output of the operational amplifier OP2 at the start of every measuring cycle as controlled by the programmer 52.

The output $V_0$ of the operational amplifier OP2 of the photocell amplifier could be applied directly to the differentiator 56 but it has been found in practice that such output contains a substantial amount of unwanted noise which is preferably removed by a low pass filter comprising an operational amplifier OP4 and a conventional second order filter network including resistors R8 and R9 and capacitors C1 and C2. Resistors R8 and R9 are connected in series between the output terminal of operational amplifier OP2 and the non-inverting input terminal of operational amplifier OP4. Capacitor C1 is connected between the non-inverting input terminal of operational amplifier OP4 and ground whereas capacitor C2 is connected between the common point of resistors R8 and R9 and the output terminal of operational amplifier OP4. The inverting input terminal of the operational amplifier is connected to its output terminal. The values of resistors R8 and R9 and capacitors C1 and C2 determine the cut-off frequency of the low pass filter. Satisfactory cancellation of noise components has been obtained with a cut-off frequency in the range of 0.1-2 Hz.

The output of the operational amplifier OP2 is also applied to signal conditioning circuit 60 (FIG. 1) which includes operational amplifier OP5 and resistors R10, R11 and R12. Resistor R10 has one terminal connected to a reference voltage V−REF and its other terminal connected to the inverting input terminal of operational amplifier OP5. Resistor R11 is a variable resistor connected between the inverting input terminal of operational amplifier OP5 and the output terminal of operational amplifier OP2. Resistor R12 is the usual feedback resistor connected between the output terminal of operational amplifier OP5 and the inverting input terminal of such amplifier. The purpose of the signal conditioning circuit is to compensate for the non-linearity of the transmittance of the reagent test paper as illustrated in FIG. 3. If this non-linearity is not compensated for, the differentiator 56 will not provide a true indication of the instantaneous concentration of the substance to be monitored as it is reacted with the reagent paper.

Referring to FIG. 4, the use of the signal conditioning circuit 60 in the feedback loop of the photocell amplifier causes the amplifier to produce a voltage output $V_O$ having the following characteristic:

$$V_O = V\ REF(T-1)/(1+kT)$$

wherein
  V REF = voltage applied to the signal conditioning circuit
  $V_O$ = output voltage of photocell amplifier
  T = transmittance or ratio of light falling on photocell 42 with respect to photocell 46
  k = R10/R11

Figure 5:
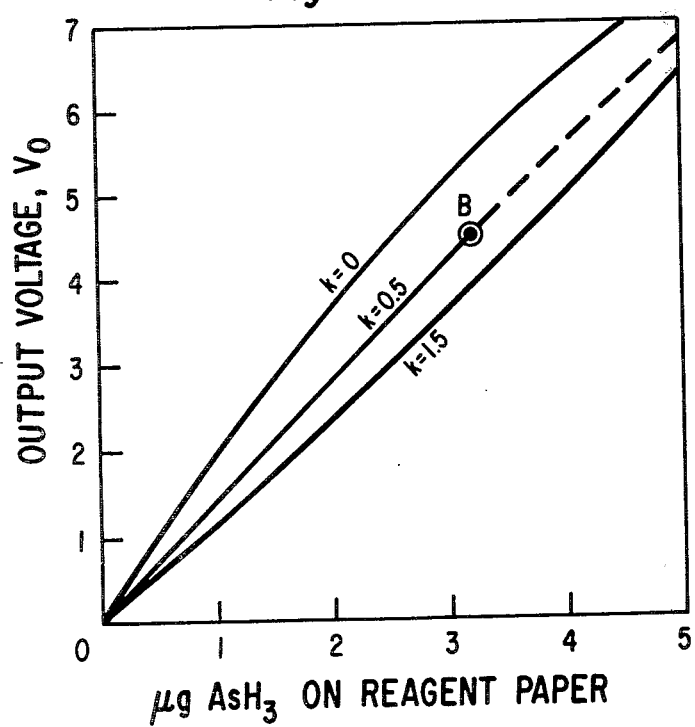
FIG. 5 illustrates the output of the photocell amplifier as a function of the amount of substance reacted with the reagent test paper with various degrees of non-linear conditioning.

As shown in FIG. 5, a number of curves have been derived for various values of k using mercury bromide as the reagent test paper for detecting arsine. The curve which is more closely linear is the one wherein k=0.5. Such curve is linear up to point B which corresponds to a transmittance value of T=0.5.

In practice, to make the output linear, a known constant concentration of the substance to be detected is continuously reacted with the reagent paper and the gain of the operational amplifier as determined by variable resistor R11 is varied until a linear ramp output is obtained.

The output of operational amplifier OP4 is applied to a differentiator circuit including operational amplifier OP6, resistor R13 and capacitor C3. Resistor R13 is connected across the inverting input terminal and the output terminal of operational amplifier OP6. Capacitor C3 is connected in series with the output terminal of operational amplifier OP4 and the inverting input terminal of operational amplifier OP6. The non-inverting terminal of the operational amplifier is connected to ground. The differentiator 56 further comprises resistor R14 connected in series with capacitor C3 and capacitor C4 connected across resistor R13. Resistor R14 and capacitor C4 act as a low pass filter for further eliminating noise components. The ratio of R13 to R14 should be 100 or more. Similarly C3 should be 100 times or more the value of C4.

The colour spots on the reagent paper decompose or fade to some extent with time and it is preferable to compensate for such decomposition. A compensation circuit including resistors R15 and R16 and variable resistor R17 is therefore provided. Resistors R15 and R17 are voltage dividers providing a fraction of $V_O$, through R16, to the non-inverting input terminal of operational amplifier OP6. The value of R16 should be the same as that of R13 so that the fraction of $V_O$ as determined by the ratio of R15 to R17 will appear at the output of the operational amplifier with opposite polarity. This compensation circuit may be adjusted by stopping circulation of the gas stream after a significant coloration of the test paper has been observed. Without compensation, the output of the differentiator will normally fall below zero as a result of colour fading of the test paper due to decomposition. Variable resistor R17 is adjusted so that the output voltage of the differentiator goes back to zero.

Although the invention has been disclosed with reference to a preferred embodiment, it is to be understood that various modifications may be made to such embodiment within the scope of the claims. For example, the signal conditioning circuit could take other forms than the previously described circuit. It could be any known exponential function operator connected between the photocell amplifier and the differentiator so as to straighten the curve of FIG. 3 and make it linear so that this linear function could be differentiated by a simple differentiator circuit for providing an indication of the instantaneous concentration of the gas being reacted with the test paper. Other types of automatic zero adjustment circuits could also be used. Similarly, other means for compensating for lamp ageing and voltage fluctuations are also envisaged. Finally, other types of photocells, amplifiers, low pass filters, decomposition compensators and differentiators could be used.

The embodiments of the invention in which an exclusive property or privilege is claimed are defined as follows:

1. An apparatus for detecting the presence of a specific substance in a gas stream comprising:
   (a) a sensing chamber adapted to receive a test paper which is stationary during a monitoring cycle and which is subject to coloration when contacted by a specific substance in a gas stream circulated through said chamber;
   (b) a light source;
   (c) means responsive to said light source for generating a light beam and directing it toward the reagent paper in the sensing chamber;
   (d) a light beam sensing device responsive to the extent to which the test paper in said sensing chamber undergoes coloration in response to exposure to the specific substance in the gas stream;
   (e) an amplifier connected to said light beam sensing device for providing an output signal which is proportional to the coloration of the test paper; and
   (f) means connected to the amplifier for providing an output which is an instantaneous indication of the concentration of the substance to be monitored, comprising a signal conditioning circuit connected to the amplifier for providing an output which is a linear function of the cumulative amount of the substance to be detected contacting the test paper, and a differentiator responsive to the output of said amplifier for deriving the instantaneous concentration of the substance in the gas stream.

2. An apparatus as defined in claim 1, further comprising a variable optical density filter, a light beam splitter for dividing said light beam into two separate beams, one directed toward the reagent test paper in the sensing chamber and the other toward said variable optical density filter, a second light beam sensing device responsive to the transmittance of said variable density optical filter, said amplifier being responsive to the two light beam sensing devices for providing an output which is a function of the ratio of the light sensed by the two light sensing devices irrespective of the light source intensity variations.

3. An apparatus as defined in claim 2 further comprising an automatic zero adjustment means including an operational amplifier connected to the output of said amplifier and a servo motor responsive to said operational amplifier and connected to said variable optical density filter for resetting the output of the amplifier to zero before making a measurement.

4. An apparatus as defined in claim 1, wherein said signal conditioning circuit is connected to the input of the amplifier and provided with positive feedback from the output of the amplifier so as to vary the input of the amplifier in a direction such as to render its output linear, whereby differentiation of the linear output of the amplifier will provide an instantaneous indication of the concentration of the substance to be detected.

5. An apparatus as defined in claim 1, further comprising a display device connected to the output of said differentiator for providing a visual indication of the concentration of the substance in the gas stream.

6. An apparatus as defined in claim 1, further comprising a low pass filter connected to the output of said amplifier for eliminating the noise components of said output signal.

7. An apparatus as defined in claim 1, further comprising a decomposition compensator interconnecting said amplifier to said differentiator for compensating for a small decomposition of the substance reacted with the test paper.

8. An apparatus as defined in claim 2, comprising a heat filter located in the light beam ahead of the beam splitter for preventing heat from the light beam from adversely affecting the test paper.

9. An apparatus as defined in claim 2, further comprising a filter located in the light beam ahead of the beam splitter for passing light of a predetermined wavelength.

10. An apparatus as defined in claim 3, wherein said test paper is in the form of a tape of predetermined length, and further comprising a motor for intermittently advancing said tape of predetermined length through the chamber prior to taking a measurement, and a programmer operative to first energize said motor for a predetermined time interval to advance the tape, then energize said automatic zero adjustment means for a second predetermined time interval to reset the amplifier to zero output, and finally initiate the measuring cycle.

11. An apparatus as defined in claim 10, wherein said automatic zero adjustment means further comprises switch means responsive to said programmer for interconnecting said operational amplifier and said servo motor.

12. An apparatus as defined in claim 2, wherein said amplifier comprises an operational amplifier having the first light sensing device connected in series with its inverting input terminal and the second light sensing device connected across its inverting input terminal and its output terminal for providing an output which is a direct ratio of the light sensed by the two light sensing devices irrespective of the light source intensity variations, a voltage reference source, a summing network for comparing the output voltage of said operational amplifier with that of the reference source, and an inverter connected to the output of said summing network for providing said output signal.

* * * * *